(12) United States Patent
Schweinert et al.

(10) Patent No.: US 7,236,561 B2
(45) Date of Patent: Jun. 26, 2007

(54) METHOD AND SYSTEM FOR ASSEMBLING AN X-RAY IMAGING SYSTEM

(75) Inventors: Gerhardt Edwin Schweinert, Cedarburg, WI (US); Ross Hoggatt, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 10/930,655

(22) Filed: Aug. 31, 2004

(65) Prior Publication Data

US 2006/0045237 A1    Mar. 2, 2006

(51) Int. Cl.
*H05G 1/60* (2006.01)
(52) U.S. Cl. .............................. 378/19; 378/4
(58) Field of Classification Search .................. 378/4, 378/19, 62, 98.8, 167; 250/370.08, 370.09
See application file for complete search history.

(56) References Cited

U.S. PATENT DOCUMENTS

| 5,799,057 | A | 8/1998 | Hoffman et al. | 378/147 |
| 6,587,538 | B2 * | 7/2003 | Igarashi et al. | 378/19 |
| 6,661,866 | B1 | 12/2003 | Limkeman et al. | 378/19 |
| 6,700,949 | B2 | 3/2004 | Susami et al. | 378/19 |
| 6,990,176 | B2 * | 1/2006 | Sherman et al. | 378/98.8 |
| 2004/0071256 | A1 | 4/2004 | Hoffmann | 378/4 |

* cited by examiner

*Primary Examiner*—Courtney Thomas
(74) *Attorney, Agent, or Firm*—Armstrong Teasdale LLP

(57) ABSTRACT

Methods and systems for assembling an X-ray imaging system are provided. The method for assembling an X-ray imaging system includes fabricating a rail that includes an arcuate member. The arcuate member includes a plurality of substantially planar facets that are circumferentially spaced about an outer periphery of the rail. The method further includes coupling a sensor array to at least one of the plurality of facets such that at least a portion of a substantially planar face of the sensor array mates in thermally conductive engagement with the facet.

26 Claims, 5 Drawing Sheets

METHOD AND SYSTEM FOR ASSEMBLING AN X-RAY IMAGING SYSTEM

BACKGROUND OF THE INVENTION

The invention relates generally to X-ray imaging systems and more particularly, to methods for assembling X-ray imaging systems.

Photodiode assemblies are used in an X-ray imaging system to produce an electrical signal representative of an attenuated X-ray beam received at a detector array of the X-ray imaging system. The performance of the photodiode assembly at least partially depends on the operating temperature of the photodiode assembly. At different operating temperatures, the photodiode assembly may produce a different electrical signal corresponding to the same intensity of the incident attenuated X-ray beam. Therefore, it is attempted to keep the photodiode assembly desirably within a narrow temperature range.

In known X-ray imaging systems, photodiode assemblies are attached to metal rails of the detector array as there is thermal conductivity between the photodiode assembly and the metal rails. However, there is a line contact between the photodiode assembly and the known metal rails as the shape of the known metal rail is a smooth arc and the planar face of the photodiode assembly is substantially planar. Further, in some know X-ray imaging systems, a highly compliant thermal material may be used between the photodiode assembly and the known metal rails to facilitate thermal coupling the photodiode assembly to the rail.

Further in known X-ray imaging systems, the detector array is skewed with respect to a focal spot of an X-ray source, to ensure a shadowing effect in an image formed by the known X-ray imaging system. However, the shadowing effect is not uniform because the ends of the skewed detector array are not equidistant from the focal spot.

BRIEF DESCRIPTION OF THE INVENTION

In one exemplary embodiment, a method for assembling an X-ray imaging system is provided. The method includes fabricating a rail that includes an arcuate member. The arcuate member includes a plurality of substantially planar facets that are circumferentially spaced about an outer periphery of the rail. The method further includes coupling a sensor array to at least one of the plurality of facets such that at least a portion of a substantially planar face of the sensor array mates in thermally conductive engagement with the facet.

In another exemplary embodiment, a computed tomographic detector array is provided. The detector array includes a plurality of sensors. Each sensor array having a substantially planar face and includes at least one X-ray sensor on the planar face of the sensor array. The detector array further includes at least one rail. The rail includes an arcuate member along the outer periphery. The arcuate member includes a plurality of planar facets circumferentially spaced about the outer periphery of the rail. The plurality of facets that meet an adjacent facet at a junction comprising at least one angle. Further, each sensor array is coupled to a respective facet.

DETAILED DESCRIPTION OF THE INVENTION

Various embodiments of the invention provide method and system for assembling an X-ray imaging system. The X-ray imaging system may be for example, a computed tomographic imaging apparatus.

Detector arrays in X-ray imaging systems typically include a rail and a plurality of sensor arrays. Further, scintillators in detector arrays generate light events when impinged by the attenuated X-ray beam. These light events are directed to photoelectrically responsive materials, such as sensor arrays in order to produce an electrical signal representative of the attenuated X-ray beam received at the detector array. In various embodiments of the invention, the sensor arrays are couples to the rail such that sensor arrays mate in thermally conductive engagement with the rail. The rail and the thermally conductive engagement between the sensor arrays and the rails is described in detail in conjunction with FIG. 1 and FIG. 2.

Figure 1:
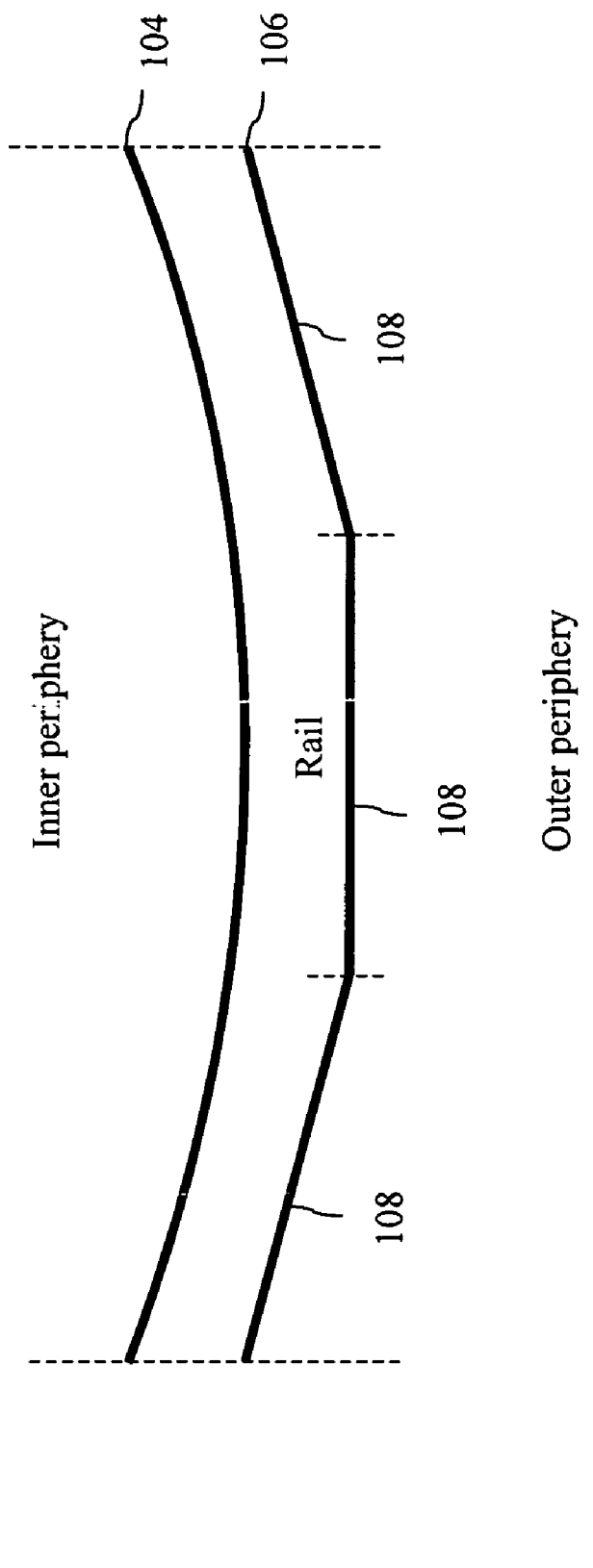
FIG. 1 is a front view of a section of a rail in accordance with an exemplary embodiment of the invention.

FIG. 1 is a front view of a section of a rail 102 in accordance with an exemplary embodiment of the invention. Rail 102 includes a curved member 104, and an arcuate member 106. In various embodiments of the invention, the material of construction of rail 102 may be stainless steel. Rail 102 has an inner periphery and an outer periphery. Curved member 104 is along the inner periphery and arcuate member 106 is along the outer periphery. Arcuate member 106 includes a plurality of facets 108. Facets 108 are substantially planar and are circumferentially spaced about the outer periphery.

In various embodiments of the invention, arcuate member 106 may be aligned, with respect to the center of curved member 104, in a manner for example, that the perpendicular bisectors of facets 108 intersect at the center of curved member 104.

In various embodiments of the invention, facet 108 meets an adjacent facet 108 at a junction comprising at least one angle. In an embodiment of the invention, the angle may be approximately one degree. In an embodiment, the junction may be machined further into a plurality of angles.

In various embodiments of the invention, length of the outer periphery of rail 102 may be typically, one meter and the radius of curved member 104 may be typically one meter. The length of facets 108 may be typically 10–15 millimeters along the outer periphery of rail 102. The width between the inner periphery of the rail 102 and the outer periphery of the rail 102 may be typically 39–40 millimeters.

In various embodiments of the invention, arcuate member 106 typically, includes fifty six to fifty seven facets 108.

It may be noted that these values are exemplary and may vary across various embodiments of the invention depending on the number of sensor arrays and structural requirements of the computed tomographic apparatus.

Figures 2, 2A:
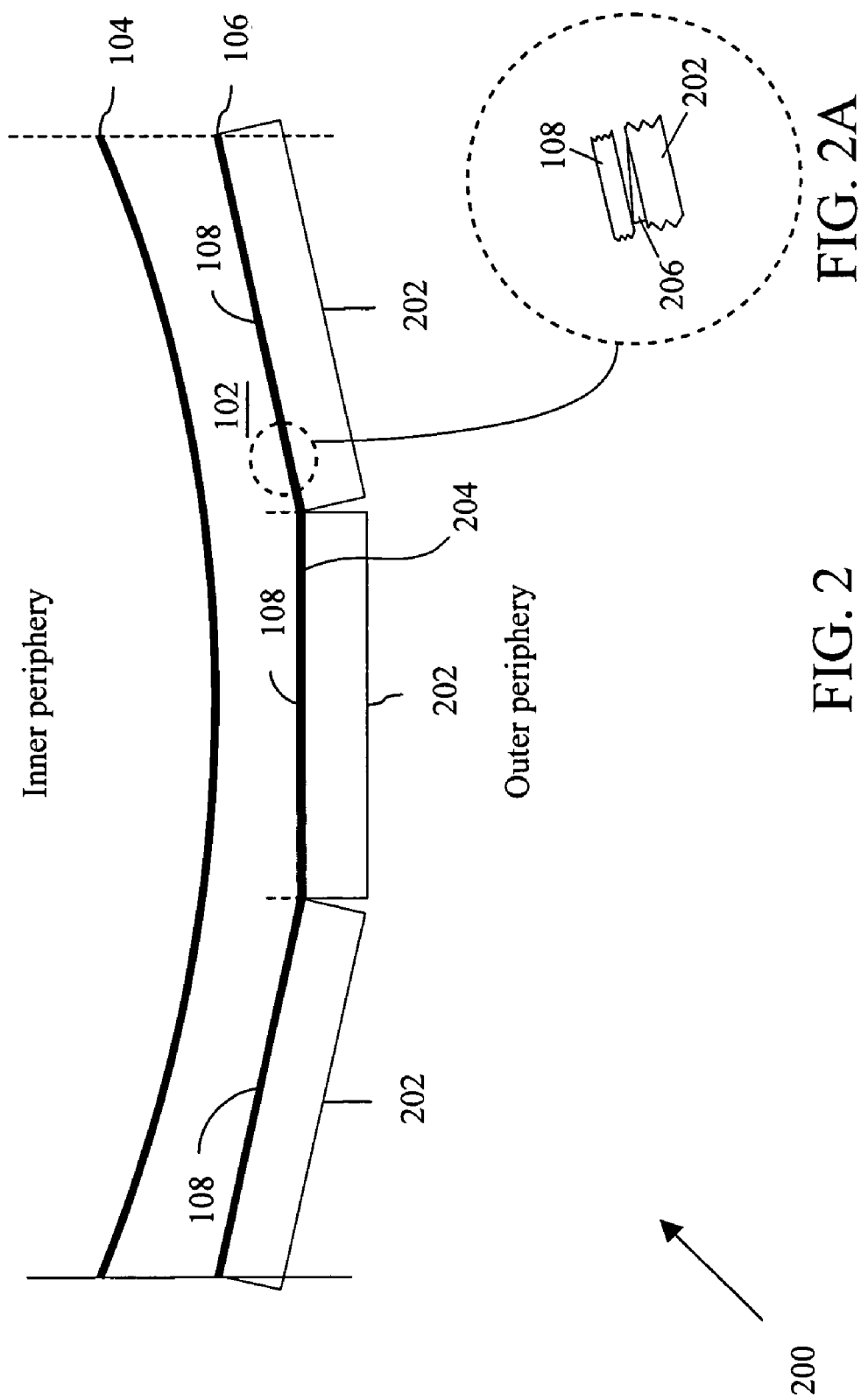
FIG. 2 is a front view of section of a detector array in accordance with an exemplary embodiment of the invention.
FIG. 2a is an enlarged view of a section of a detector array in accordance with an exemplary embodiment of the invention.

FIG. 2 is a front view of section of a detector array 200 in accordance with an exemplary embodiment of the invention. FIG. 2a is an enlarged view of a section of a detector array in accordance with an exemplary embodiment of the invention. In various embodiments of the invention, detector array 200 may be, for example, a computed tomographic detector array. Detector array 200 includes a plurality of sensor arrays 202 and at least one rail 102.

Sensor arrays 202 may be photo responsive materials and have a substantially planar face. In various embodiments of the invention, sensor arrays 202 may be, for example, photomultipliers or photodiode assemblies. Sensor arrays 202 include at least one X-ray sensor on planar faces of sensor arrays 202. The X-ray sensors of sensor arrays 202 may be exposed to the light event. In various embodiments of the invention, sensor arrays 202 are coupled to rail 102 such that sensor arrays 202 mate in thermally conductive engagement with rail 102.

In an embodiment of the invention, the planar face of sensor arrays 202 is coupled to facets 108 about the outer periphery of rail 102, such that thermal conduction may occur. In another embodiment of the invention, the X-ray sensors of sensor arrays 202 are coupled to facets 108 about the outer periphery of rail 102, such that thermal conduction may occur. In various embodiments of the invention, a thermally conductive film 204 is positioned between the planar face of sensor arrays 202 and facets 108. Thermally conductive film 204 has a predetermined heat conduction coefficient and may include a pressure sensitive adhesive. The thickness of thermally conductive film 204 may be in the range of 25–250 micrometers and all sub-ranges there between. Exemplary thermally conductive films may be dead soft Aluminum tapes such as 3M™ Aluminum foil tape 425 and 431. 3M™ is a registered trademark of 3M Company. The thermally conductive engagement between sensor arrays 202 and rail 102 ensures sensor arrays 202 are maintained within a narrow temperature range during scanning. The narrow temperature range may be typically 2–4° and all sub-ranges there between.

In various embodiments of the invention, sensor array 202 are coupled to respective facet 108 through an intermediate element 206 positioned between sensor array 202 and respective facet 108. Intermediate element 206 has a predetermined cross-section such that at least a portion of the face of the sensor array mates in thermal engagement with at least a portion of respective facets 108. The material of construction of intermediate element 206 may be a thermally conductive metal such as stainless steel and aluminum.

In various embodiments of the invention, arcuate member 106 may be aligned, with respect to a center of curved member 104, in a manner for example, that facets 108 may be perpendicular to a tangent of a circle (of a predetermined radius) concentric with the center of curved member 104.

In various embodiments of the invention, arcuate member 106 may be aligned, with respect to the center of curved member 104, in a manner for example, that the perpendicular bisectors of facets 108 may be tangents to the circle (of the predetermined radius) concentric with curved member 104. Facets 108 of arcuate member 106 may be skewed by typically, 0.13°–0.2° and all sub-ranges there between, with respect to the center of curved member 104. The predetermined radius of the circle concentric with the center of curved member 104 is dependent on the skew angle. In various embodiments of the invention, adjacent facets 108 may be joined through a transition element positioned between adjacent facets 108. In various embodiments of the invention, the transition element may be planar or curved in shape. The angle between the transition element and adjacent facets 108 may be between 0.5° and 1° and the length of the transition element may be in the range of 0.5–3 millimeters and all sub-ranges there between. In various embodiments of the invention, the material of construction of the transition element is stainless steel.

In various embodiments of the invention, sensor arrays 202 mate in thermally conductive engagement with skewed facets 108 of arcuate member 106. This ensures a uniform shadowing effect in the image formed by computed tomographic apparatus.

Figure 3:
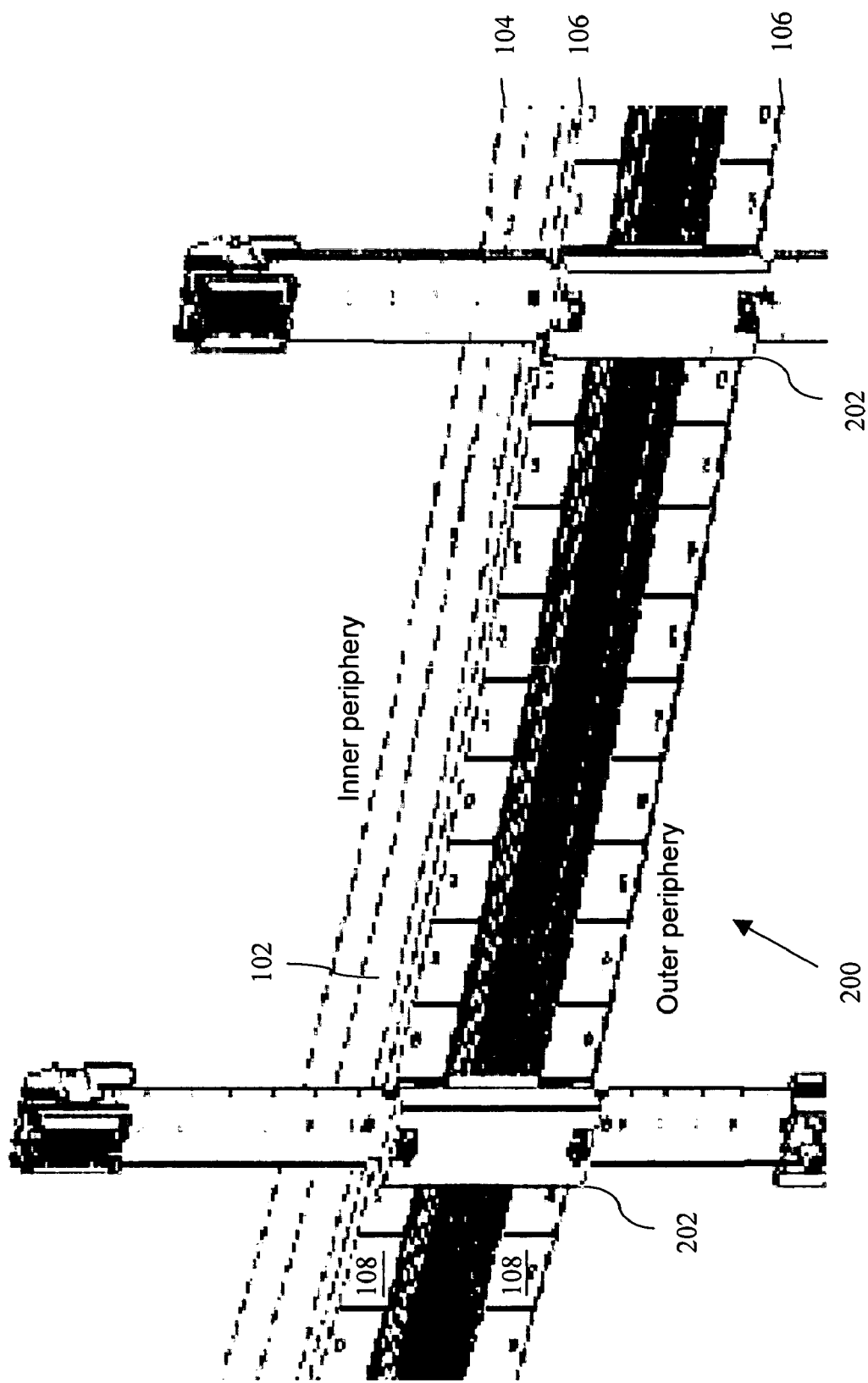
FIG. 3 shows a section of a detector array in accordance with another embodiment of the invention.

FIG. 3 shows a section of Detector array 200 in accordance with another embodiment of the invention. Detector array 200 includes a second rail 102. Second rail 102 includes curved member 104 and arcuate member 106. Second rail 102 is positioned parallel to rail 102 such that the second rail 102 is exactly below rail 102. Sensor arrays 202 spans the gap between arcuate member 106 of rail 102 and arcuate member 106 of second rail 102 such that the planar faces of sensor arrays 202 mates in thermally conductive engagement with facets 108 of rail 102 and facets 108 of second rail 102. The gap between arcuate member 106 of rail 102 and arcuate member 106 of second rail 102 may be typically 30–300 millimeters and all sub-ranges there between.

Figure 4:
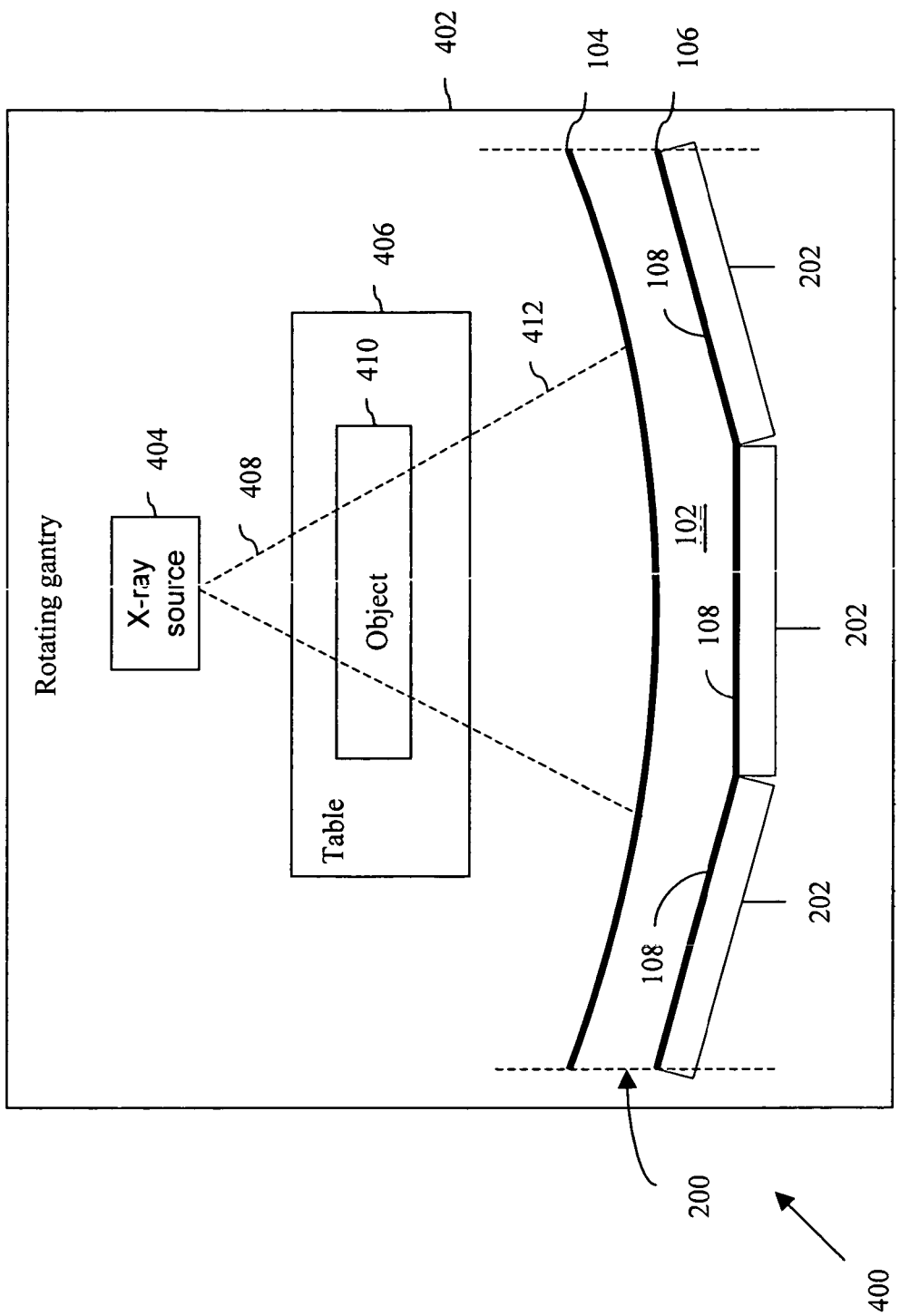
FIG. 4 is a block diagram of a computed tomographic imaging apparatus in accordance with an exemplary embodiment of the invention.

FIG. 4 is a block diagram of a computed tomographic imaging apparatus 400 in accordance with an exemplary embodiment of the invention. Computed tomographic apparatus 400 includes a rotating gantry 402. Rotating gantry 402 includes an X-ray source 404 spaced diametrically across a viewing area from Detector array 200. A table 406 is configured to support an object 410, such as a patient within the viewing area during a scan. X-ray source 404 projects an X-ray beam 408 that passes through object 410. Object 410 is being scanned to form an image and is supported by table 406. Object 410 may be, for example, a patient. X-ray beam 408 passes through object 410 and may be attenuated by interactions with object 410 that reduce the flux of X-ray beam 408. Detector array 200 then detects an attenuated X-ray beam 412. The inner periphery of rail 102 is exposed to attenuated X-ray beam 412 and is the active side of computed tomographic imaging apparatus 400.

Figure 5:
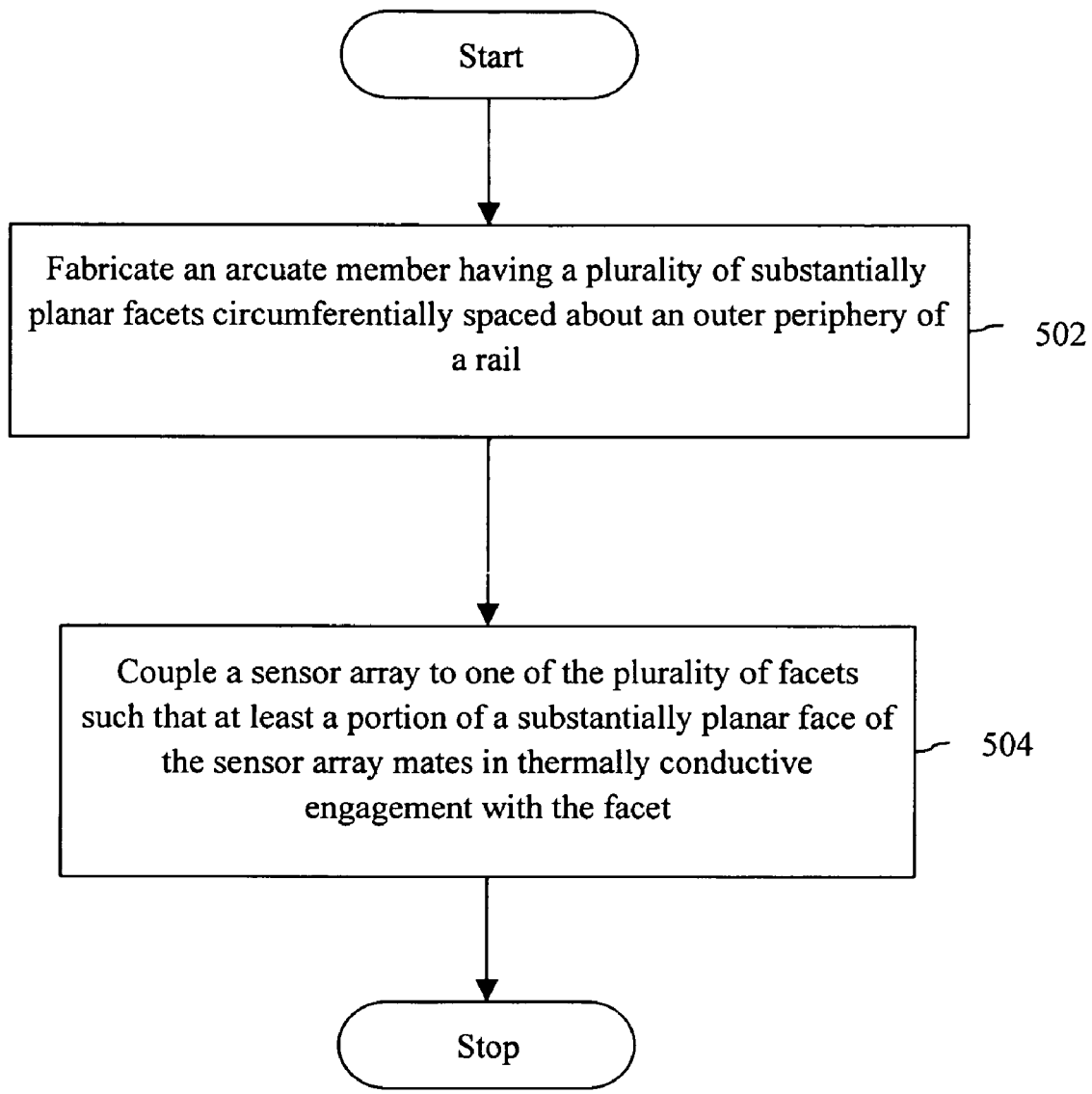
FIG. 5 is a flowchart illustrating a method for assembling an X-ray imaging system in accordance with an exemplary embodiment of the invention.

FIG. 5 is a flowchart illustrating a method for assembling an X-ray imaging system in accordance with an exemplary embodiment of the invention. In various embodiments of the invention, X-ray imaging system may be computed tomographic apparatus 400.

At 502, arcuate member 106 is fabricated. In various embodiments of the invention, arcuate member 106 is machined such that facets 108 meet at a junction comprising at least one angle. In various embodiments of the invention, arcuate member 106 is machined such that facets 108 may be perpendicular to a tangent of the circle (of the predetermined radius) concentric with the center of curved member 104.

In various embodiments of the invention, second rail 102 is positioned parallel to rail 102.

At 504, sensor array 202 is coupled to one of plurality of facets 108 such that at least a portion of a substantially planar face of sensor array 202 mates in thermally conductive engagement with one of facets 108. Sensor array 202 is coupled to one of plurality of facets 108 using a fastener such as screw. In an embodiment of the invention, the X-ray sensor of sensor array 202 are coupled to one of plurality of facets 108 about the outer periphery of rail 102, such that thermal conduction may occur.

In various embodiments of the invention, a thermally conductive film is positioned between the planar face of sensor array 202 and facets 108.

In various embodiments of the invention, sensor array 202 spans the gap between arcuate member 106 of rail 102 and arcuate member 106 of second rail 102 such that the planar face of sensor array 202 mates in thermally conductive engagement with one of facets 108 of rail 102 and corresponding facet 202 of second rail 102.

The various embodiments of the invention provide an X-ray imaging system facilitates maintaining the sensor arrays within a narrow temperature range during scanning. Further, the various embodiments of the invention provide an X-ray imaging system that ensures a uniform shadowing effect by skewing facets of an arcuate member of a rail.

While the invention has been described in terms of various specific embodiments, those skilled in the art will recognize that the invention can be practiced with modification within the spirit and scope of the claims.

What is claimed is:

1. A method for assembling an X-ray imaging system, said method comprising:

fabricating a rail comprising an arcuate member and a curved member defined by a radius extending from a center of the curved member, wherein the arcuate member and curved member are oriented such that the curved member defines an inner periphery of the rail and the arcuate member defines an outer periphery of the rail, and wherein the arcuate member includes a plurality of substantially planar facets circumferentially spaced about the outer periphery of the rail; and coupling a sensor array to at least one of the plurality of facets such that at least a portion of a substantially planar face of the sensor array mates in thermally conductive engagement with the facet.

2. A method in accordance with claim 1 wherein fabricating an arcuate member comprises machining the arcuate member to create a facet on the outer periphery of the rail, the facet configured to be substantially perpendicular to a radial of the arcuate member.

3. A method in accordance with claim 1 wherein fabricating an arcuate member comprises machining the arcuate member to create at least one facet on the outer periphery of the rail, the facet configured to be substantially perpendicular to a tangent of a circle circumscribing a center of the arcuate member, the circle having a predetermined radius from the center of the arcuate member.

4. A method in accordance with claim 1 wherein fabricating an arcuate member comprises machining the arcuate member to create at least one facet on the outer periphery of the rail, a perpendicular bisector of the at least one facet being tangent to a circle of a predetermined radius, the circle being concentric with the arcuate member of the rail.

5. A method in accordance with claim 1 wherein fabricating an arcuate member comprises fabricating an arcuate member having a plurality of planar facets that meet at a junction having at least one angle.

6. A method in accordance with claim 1 wherein coupling a sensor array to one of the plurality of facets comprises facilitating thermal conduction between the sensor array and the facet.

7. A method in accordance with claim 6 wherein facilitating thermal conduction between the sensor array and the facet comprises and positioning a thermally conductive film, having a predetermined heat conduction coefficient, between the sensor array and the facet.

8. A method in accordance with claim 1 wherein coupling a sensor array to at least one of the plurality of facets further comprises:

positioning a second rail comprising a second fabricated arcuate member parallel to the arcuate member; and coupling the sensor array to the second arcuate member such that the sensor array spans a gap defined between the arcuate member and the second arcuate member, and such that at least a portion of a substantially planar face of the sensor array mates in thermally conductive engagement with a respective facet of the second arcuate member.

9. A method in accordance with claim 8 wherein positioning a second fabricated arcuate member parallel to the arcuate member comprises positioning a second fabricated arcuate member having a plurality of substantially planar facets circumferentially spaced about an outer periphery of the second rail parallel to the arcuate member.

10. A computed tomographic detector array configured to detect X-rays passing through an object, said detector array comprising:

a plurality of sensor arrays, each sensor array having a substantially planar face and comprising at least one X-ray sensor on the planar face of the sensor array; and at least one rail comprising an arcuate member defining an outer periphery and a curved member defining an inner periphery of said at least one rail, said curved member defined by a radius extending from a center of said curved member, said arcuate member and said curved member are aligned with respect to said center, said arcuate member comprising a plurality of planar facets circumferentially spaced about the outer periphery, said plurality of planar facets meet an adjacent facet at a junction comprising at least one angle, each sensor array coupled to a respective facet.

11. A computed tomographic detector array in accordance with claim 10 wherein said plurality of planar facets are circumferentially spaced about said rail outer periphery.

12. A computed tomographic detector array in accordance with claim 10 wherein said plurality of planar facets are configured to be substantially perpendicular to a tangent of a circle circumscribing a center of the arcuate member, the circle having a predetermined radius from the center of the arcuate member.

13. A computed tomographic detector array in accordance with claim 10 wherein said plurality of planar facets are configured such that a perpendicular bisector of the at least one facet is tangent to a circle of a predetermined radius, the circle being concentric with the arcuate member of the rail.

14. A computed tomographic detector array in accordance with claim 10 wherein each sensor array is directly coupled to a respective facet such that at least a portion of the face of the sensor array mates in thermal communication with at least a portion of a complementary planar portion of the facet.

15. A computed tomographic detector array in accordance with claim 10 wherein each sensor array is coupled to a respective facet through a intermediate element having a predetermined cross-section such that at least a portion of the face of the sensor array mates in thermal communication with at least a portion of a complementary planar portion of the facet.

16. A computed tomographic detector array in accordance with claim 10 further comprising a pair of rails oriented in parallel with respect to each other, each of the facets of one rail corresponding to a facet of the other rail.

17. A computed tomographic detector array in accordance with claim 16 wherein each sensor array is directly coupled to corresponding facets on each of the pair of rails such that at least a portion of the face of the sensor array mates in thermal communication with at least a portion of a complementary planar portion of each corresponding facet.

18. A computed tomographic imaging apparatus comprising:
   a rotating gantry;
   an X-ray source on the rotating gantry configured to project an X-ray beam through an object being imaged;
   a table configured to support the object in the X-ray beam; and
   a detector array on the rotating gantry configured to detect X-rays passing through the object, said detector array comprising a plurality of sensor arrays, each sensor array having a substantially planar face and comprising at least one X-ray sensor on an active side configured to detect X-rays, each sensor array coupled to at least one arcuate rail, said rail comprising an arcuate member and a curved member, said arcuate member comprising a plurality of planar facets that meet at a junction comprising at least one angle, said curved member defined by a radius extending from a center of said curved member.

19. A computed tomographic imaging apparatus in accordance with claim 18 wherein said plurality of planar facets are circumferentially spaced about the outer periphery of said rail.

20. A computed tomographic imaging apparatus in accordance with claim 18 wherein each sensor array is directly coupled to a respective facet such that at least a portion of the active face of the sensor array mates in thermal communication with at least a portion of a complementary planar portion of the facet.

21. A computed tomographic imaging apparatus in accordance with claim 18 further comprising a pair of rails oriented in parallel with respect to each other, each of the facets of one rail corresponding to a facet of the other rail.

22. A computed tomographic imaging apparatus in accordance with claim 21 wherein each of the facets of one rail lays in the same plane as the corresponding facet of the other rail.

23. A computed tomographic imaging apparatus in accordance with claim 22 wherein each sensor array is directly coupled to corresponding facets on each of the pair of rails such that at least a portion of the active face of the sensor array mates in thermal communication with at least a portion of a complementary planar portion of each corresponding facet.

24. A computed tomographic imaging apparatus in accordance with claim 18 further comprising a pair of rails oriented in parallel with respect to each other, each rail comprising a plurality of planar facets wherein each of the facets of one rail corresponds to a facet of the other rail, each facet defined on the outer periphery of one of the pair of rails, the facet configured to be substantially perpendicular to a radial of the respective rail.

25. A computed tomographic imaging apparatus in accordance with claim 18 further comprising a pair of rails oriented in parallel with respect to each other, each rail comprising a plurality of planar facets wherein each of the facets of one rail corresponds to a facet of the other rail, each facet defined on the outer periphery of one of the pair of rails, each facet configured to be substantially perpendicular to a tangent of a circle circumscribing a center of the arcuate member, the circle having a predetermined radius.

26. A computed tomographic detector array in accordance with claim 25 wherein said plurality of planar facets are configured such that a perpendicular bisector of the at least one facet is tangent to a circle of a predetermined radius, the circle being concentric with the curved member of the rail.

* * * * *